(12) United States Patent
Akkara et al.

(10) Patent No.: US 6,228,997 B1
(45) Date of Patent: *May 8, 2001

(54) TRANSESTERIFICATION OF INSOLUBLE POLYSACCHARIDES

(75) Inventors: Joseph A. Akkara, Holliston; David L. Kaplan, Stow; Ferdinando F. Bruno, Andover, all of MA (US); Jonathan S. Dordick, Iowa City, IA (US)

(73) Assignee: The United States of America as represented by the Secretary of the Army, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/192,209

(22) Filed: Jul. 10, 1998

Related U.S. Application Data

(63) Continuation of application No. 08/774,329, filed on Jul. 10, 1998, now Pat. No. 6,063,916.

(51) Int. Cl.[7] ............ C08B 37/08; C08B 13/00; C08B 37/16
(52) U.S. Cl. ............ 536/20; 536/124; 536/66; 536/103; 536/116
(58) Field of Search ............ 536/58, 66, 69, 536/103, 112, 114, 116, 119, 123, 123.1, 124, 20

(56) References Cited

U.S. PATENT DOCUMENTS

| | | | |
|---|---|---|---|
| 4,443,595 | * | 4/1984 | Namikoshi et al. ............ 536/58 |
| 4,614,780 | | 9/1986 | Huhn et al. . |
| 4,624,919 | | 11/1986 | Kokusho et al. . |
| 4,839,287 | | 6/1989 | Holmberg et al. . |
| 5,141,860 | | 8/1992 | Bomemann et al. . |
| 5,474,915 | | 12/1995 | Dordick et al. . |
| 5,480,787 | | 1/1996 | Negishi et al. . |
| 5,486,508 | * | 1/1996 | Uda et al. ............ 514/58 |
| 5,508,048 | | 4/1996 | Padey . |
| 5,508,182 | | 4/1996 | Schneider et al. . |

OTHER PUBLICATIONS

Mayer, J.M., Kaplan, D.L., 2 Trends Polym. Sci. 227 (1994).
Klibanov, A.M., 14 Trends Biocem. Sci. 141 (1989).
Klibanov, A.M., 23 Acc. Chem. Res. 114 (1990).
Bruno, F.F.; Akkara, J.A.; Kaplan, D.L.; Gross, R.; Swift, G.; Dordick, J.S.; 28 Macromolecules 8881 (1995).
Dordick, J.S., 11 Microb. Technol. 194 (1989).
Kuhl, P., Haling, P.J., Jakubke, H.D., 31 Tetrahedron Lett. 5213 (1990).
Gill, I., Vulfson, E.J., 115 J. Am. Chem. Soc. 3348 (1994).
Paradkar, V.M., Dordick, J.S., 116 J. Am. Chem. Soc. 5009 (1994).
Lukaszewski, G.M., 15 Lab. Practice 551 (1966).
Itoh, T., Tsujii, Y., Suzuki, H., Fukuda, T., Miyamoto, T., 24 Polym. J. 641 (1992).

* cited by examiner

*Primary Examiner*—Howard C. Lee
(74) *Attorney, Agent, or Firm*—Vincent J. Ranucci

(57) ABSTRACT

*Bacillus subtilis* protease catalyzes the acylation of organic solvent-insoluble polysaccharides in isooctane solution containing vinyl esters of fatty acids as acyl donor. The reaction occurs only when the enzyme is solubilized via ion-pairing with the anionic surfactant dioctyl sulfosuccinate, sodium salt (AOT). Enzyme based acylation was demonstrated with amylose, cyclodextrins, cellulose, cellulose derivatives, and other polysaccharides such as chitosan, pullulan, and maltodextrose. These polysaccharides are reactive either as a cryogenically milled powder suspended in the organic solvent or as a thin film deposited onto ZnSe slides. For chitosan, α-cyclodextrin, and hydroxyethyl cellulose (HEC), the enzymatic crosslinking reaction occurs using adipic acid divinyl ester (C6DVE). HEC forms a compound that gels in solvents such as ethyl alcohol and dimethyl sulfone oxide (DMSO). Electron spectroscopy chemical analysis (ESCA) of the first 100 Å of the amylose thin film amylose indicates that the acylated surface had a degree of substitution of 0.9±0.1 acyl chains per glucose moiety and this corresponded well to the expected regioselectivity of subtilisin catalysis on glucose-containing compounds. $^1$H-NMR studies indicated that only the C-6 hydroxyl groups of the glucose moiety were acylated with amylose and γ-cyclodextrin. However, β-cyclodextrin, and α-cyclodextrin were modified at secondary alcohols and at all three alcohols, respectively. This approach represents the first attempt at using enzymes to modify organic solvent-insoluble polymers in nonaqueous media.

3 Claims, 4 Drawing Sheets

$CH_3(CH_2)_8COOCH=CH_2 \; CH_3CHO$

Where for  $n=6 \; (\alpha)$    $R_1, R_2, R_3 = CH_3(CH_2)_8CO$ $n=7 \; (\beta)$    $R_1 = OH, R_2, R_3 = CH_3(CH_2)_8CO$ $n=8 \; (\gamma)$    $R_1 = CH_3(CH_2)_8CO \; R_2, R_3 = OH$ $n=1000 \pm 100$ (amylose)  $R_1 = CH_3(CH_2)_8CO \; R_2, R_3 = OH$

TRANSESTERIFICATION OF INSOLUBLE POLYSACCHARIDES

This application is a continuation of application Ser. No. 08/774,329 filed on Jul. 10, 1998, now U.S. Pat. No. 6,063,916.

STATEMENT OF GOVERNMENT INTEREST

The invention described herein may be manufactured and used by the Government for governmental purposes without the payment of any royalty thereon.

FIELD OF THE INVENTION

The present invention relates generally to the enzyme-catalyzed acylation of insoluble polysaccharides.

BACKGROUND OF THE INVENTION

Selective acylation of polysaccharides is desirable to tailor their structural and functional properties, hydrophobicity and hydrophilicity, interfacial properties, and biocompatibility. E.g., fatty acid esters of saccharides and polysaccharides may be useful as bioerodable drug delivery matrices, and biodegradable emulsifiers, compatibilizers, and detergents.[1] However, selective acylation of polysaccharides by chemical reactions are difficult due to the lack of specificity, solubility, and the multifunctionality of the polymer.[2] Enzymes have been used to acylate saccharides (up to 5 glucose moiety) regioselectively under mild conditions in organic solvents.[2-4] Similar reactions with polysaccharides would be desirable. However, the lack of solubility of these polymers and the enzymes in organic solvents implies significant problems in carrying out these conversions. Accordingly, alternative methods of achieving a functionally significant degree of acylation are required.[5-7]

Enzymes are powerful catalysts in organic solvents where they catalyze a wide variety of reactions that are difficult to perform in aqueous solutions. This is particularly evident in transesterification reactions catalyzed by lipases and proteases wherein a variety of nucleophiles act as substrates for enzyme-catalyzed acyl transfer in nearly anhydrous organic solvents. Unfortunately, many polyhydroxylated compounds are either sparingly soluble in only the most polar organic solvents, or are completely insoluble in organic media. For these substrates, conventional non-aqueous enzymology is unable to support catalytic transformations. The development of a suitable technique for the selective modification of polysaccharides in organic solvents, therefore, would represent both an opportunity for the synthesis of novel materials as well as a means to overcome a technical hurdle in the broader uses of enzymes in non-aqueous media.

Accordingly, it is an object of this invention to overcome the above illustrated inadequacies and problems of insoluble polysaccharides by providing an improved method of their transesterification.

It is another object of this invention to provide a method of acylating polysaccharides wherein their selective modification results in structural and/or functional benefits.

Yet another object of the present invention is to provide a method of enabling the use of enzymes to catalyze reactions in non-aqueous media for the synthesis of bioerodable and biocompatible compounds.

SUMMARY OF THE INVENTION

The present invention provides processes for the production of polysaccharides esterified regioselectively in position C6 or, for the case of cyclodextrins, in position C2 and C3. Such attribute are novel because chemical esterification is unable to modify regioselectively such macromolecules. The processes also emphasize recycling of the reaction media leading to waste minimization, mild reaction conditions, and minimal byproduct formation. Isooctane and the solubilized enzyme can be easily regenerated to minimize product cost and environmental hazard.

Recently, a method was developed to solubilize enzymes in hydrophobic organic solvents through the formation of enzyme-surfactant ion pairs.[8] These ion-paired, organic-soluble enzymes are extremely active in hydrophobic solvents, such as isooctane. The present invention demonstrates that polysaccharides and cyclic oligosaccharides such as amylose, chitosan, pullulan, maltodextrose, cellulose, hydroxypropyl cellulose (HPC), hydroxyethyl cellulose (HEC), hydroxymethyl cellulose (HMC), α-, β-, γ-cyclodextrins and similar polysaccharides when deposited as a thin film or cryogenically milled can be regioselectively acylated by catalysis in organic solvents using an organic-soluble enzyme preparation of subtilisin (from *Bacillus subtilis*). This represents the first attempt at catalyzing solvent-insoluble polymer modification using enzymes in organic solvents.

Proteases such as subtilisin (from *Bacillus subtilis*), ion paired with AOT, remained predominantly active and soluble in isooctane. To enhance the reactivity of insoluble substrates, thin films and cryogenically milled powders of amylose, chitosan, pullulan, maltodextrose, cellulose, hydroxypropyl cellulose (HPC), hydroxyethyl cellulose (HEC), hydroxymethyl cellulose (HMC), α-, β-, γ-cyclodextrins and similar polysaccharides were prepared to increase surface area. All these polysaccharides were esterified and some of these biopolymers were selectively transesterified using an ion-paired protease. α-Cyclodextrins were also non-selectively transesterified. Chitosan, pullulan, maltodextrose, cellulose, hydroxypropyl cellulose (HPC), and hydroxymethyl cellulose (HMC) were also transesterified enzymatically with the same methodology.

Modified polysaccharides can be used for biodegradable emulsifiers, compatibilizers, and detergents. Of particular importance is the potential broad use of these low cost polymers for edible wrapping film utilized for food storage. In addition to the above applications, esterified polysaccharides can be of extreme interest to the paper industry in order to efficiently recycle paper and other compounds based on cellulose. Other application can be envisioned in the manufacturing of drug delivery systems, specific filters, high absorbance compounds.

Other objects, features and advantages will be apparent from the following detailed description of preferred embodiments thereof taken in conjunction with the accompanying drawings.

DETAILED DESCRIPTION OF EMBODIMENTS

Figure 1A:
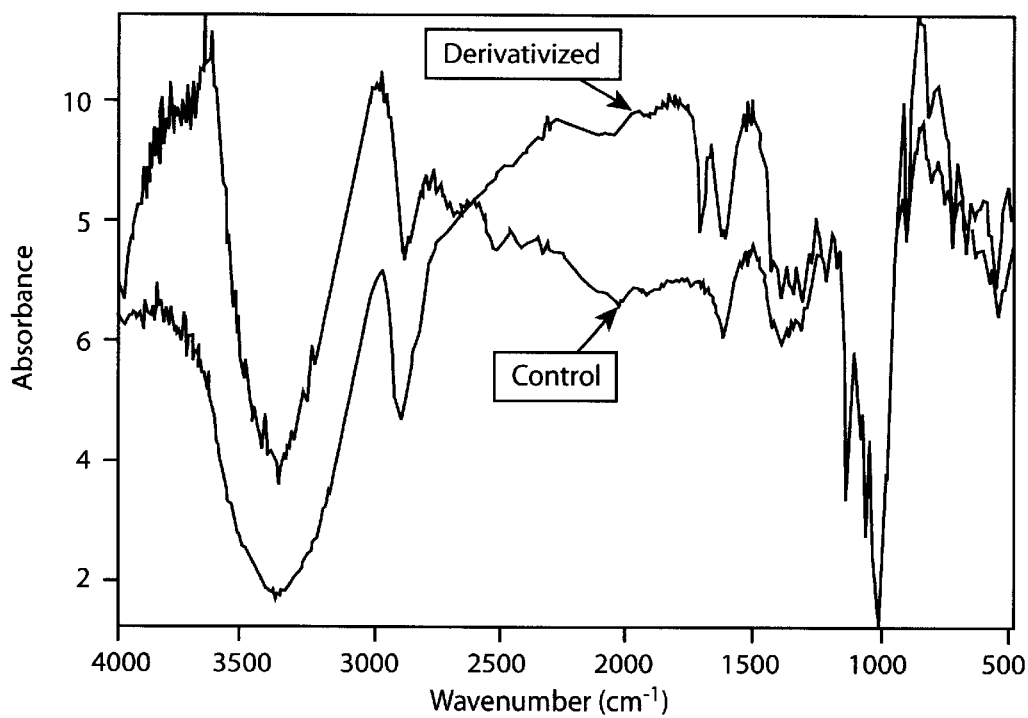
FIG. 1A shows FTIR spectra of control and derivatized γ-cyclodextrin.

The enzymatic process described herein can be envisioned as a new method for the synthesis and regioselective modification of polysaccharides and oligosaccharides in nonaqueous media, even when the substrate is insoluble in the organic solvent. This approach is amenable to a wide range enzymes and acyl donors. Moreover this technique is capable to derivatize other polysaccharides and hydroxylated polymers, such as chitosan, pullulan, maltodextrose, cellulose, hydroxypropyl cellulose (HPC), hydroxyethyl cellulose (HEC), hydroxymethyl cellulose (HMC), hydroxymethylethyl cellulose (HMEC), etc.

Preparatory to experimental verification of the present invention, *Bacillus subtilis* (1.1 mg/mL, Protease N) was dissolved in N-[2-hydroxyethyl]piperazine-N'-[2-ethanesulfonic acid] (HEPES) or 1,3-bis[tris (hydroxymethyl)-methylamino] propane (BTP) buffer (10 mM, pH 7.8) containing 6 mM KCl. The aqueous solution was mixed with an equal volume of isooctane containing 2 mM dioctylsulfosuccinate, sodium salt (AOT) and the bi-phasic solution at 25° C. was stirred at 250 rpm. After 30 minutes the phases were allowed to separate and the organic phase was removed.[7] The protein and the water content of the isooctane solution were determined by absorbance at 280 nm and Karl-Fischer titration, respectively. Based on the measurements, approximately 1.0 mg/mL of enzyme was in the isooctane solution with a water content of <0.01% (v/v).

For the formation of the film, 10 mg of each polysaccharides were dissolved in 100 mL boiling water. The solution was poured in a beaker where was placed a ZnSe slide. The water was dried out by evaporation and the polymers were deposited onto ZnSe slide (2.54 cm×2.54 cm×0.1 mm) as a thin film (estimated film thickness 1000μ). The acylation was then performed, as set forth in the examples below.

EXAMPLE 1

A solution that contained a 40-fold molar excess of the vinyl ester (n-capric vinyl ester (C10VE), n-caproic vinyl ester (C6VE), or n-butyric vinyl ester (C4VE)) relative to the polysaccharide's hydroxyl groups, was pipetted onto a thin layer of non-acylated polysaccharide deposited onto ZnSe slides. The reaction was allowed to proceed in the absence of shaking for 48 h at 37° C. at which time it was terminated by removing the solid polymer and washing it with fresh isooctane to remove unreacted vinyl ester.

EXAMPLE 2

The transesterification was also conducted using cryogenically milled polysaccharides. A similar procedure as for the film form, above, was used for the powder form, except that the reaction was performed in the presence of shaking (350 rpm). Here amylose is reported as an example. The polymer powder had a particle size of less than 100 μm. The surface area to weight ratio was 546 cm²/g. The enzymatic transesterification reaction was initiated by adding 60 mM of the vinyl fatty acids, such as n-capric acid vinyl ester (C10VE), n-caproic acid vinyl ester (C6VE) or n-butyric acid vinyl ester (C4VE), to the isooctane solution solubilized protease from *Bacillus subtilis* and the polysaccharides in powder form.

EXAMPLE 3

The enzymatic transesterification was also conducted using adipic acid divinyl ester (C6DVE) in presence of chitosan, α-cyclodextrin, and hydroxyethyl cellulose (HEC) in powder form. A procedure similar to example 2, above, was used. Here chitosan is reported as an example. The polymer powder had a particle size less than 100 μm. The surface area was 546 cm²/g. The enzymatic transesterification and crosslinking reaction was initiated by adding 60 mM of the adipic acid divinyl ester (C6DVE) to the isooctane solution containing solubilized protease and the polysaccharides in powder form.

RESULTS

The products were dried overnight and used for analytical assessment. Fourier Transformer Infrared (FTIR) spectra of the films were collected on an FT-Raman 7600 and the number of scans was 8500. $^1$H-NMR was assessed on FT-NMR 250 MHz. The samples were dissolved in DMSO-d6 and the concentrations were of 5 mg/mL. Thermogravimetric analysis (TGA) was conducted on a TGA 9500 and the sample size ranged between 5–10 mg. The rate of temperature increase was of temperature increase was of 10° C./min. Electron Spectroscopy Chemical Analysis (ESCA) of the first 100 Å of the amylose thin film amylose was performed.

Figure 3:
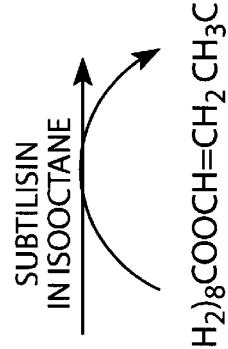
FIG. 3 shows proposed schematics for the transesterification reaction of α-, β, γ-cyclodextrin and amylose prepared by subtilisin catalysis in isooctane.
Figure 3:
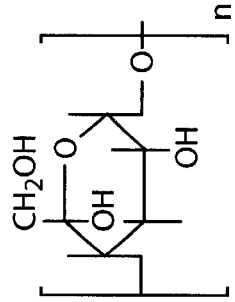
Figure 3:
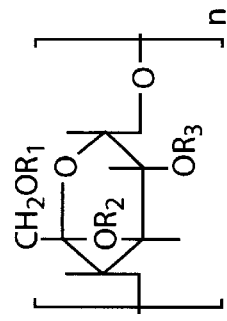

$^1$H-NMR was used to determine the position of enzymatic acylation of amylose. In comparison to underivatized amylose, there was a significant shift in the 6-hydroxyl proton and a change in the peak area. Thus, subtilisin appears to be highly efficient in catalyzing the regioselective acylation of nearly all primary hydroxyl groups on amylose polymers. FIG. 3 depicts the proposed structure of the modified amylose.

Figure 1B:
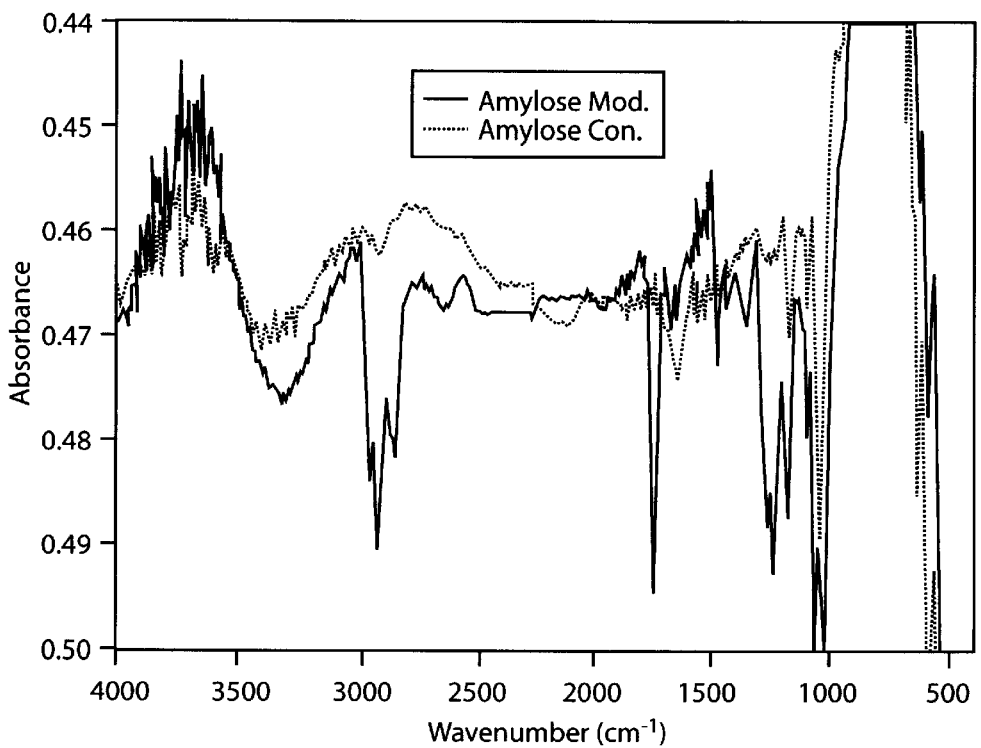
FIG. 1B shows FTIR spectra of control and derivatized amylose.

The results for the γ-cyclodextrin and of the amylose enzymatic modification illustrate the general principles of the present invention. As shown if FIGS. 1A and 1B, the enzymatic reaction resulted in transesterification of γ-cyclodextrin and amylose with an FTIR spectrum that contained large absorption peaks at 2920 and 2850 cm$^{-1}$ (corresponding to the C—H stretch of an alkyl chain) and a peak in the region 1693–1737 cm$^{-1}$, corresponding to a C=O of an ester group. The carbonyl peak was not present in the unmodified amylose or γ-cyclodextrin or in control experiments when γ-cyclodextrin or amylose were treated with the vinyl esters in the absence of enzyme. Moreover, no vinyl group was present in the modified polysaccharides as determined by the lack of absorbance at 871 and 951 cm$^{-1}$ in the FTIR spectrum. Thus, adsorption of the vinyl esters to the polymer during the reaction does not occur. Our studies with α-cyclodextrin, β-cyclodextrin, chitosan, pullulan, maltodextrose, cellulose, hydroxypropyl cellulose (HPC), hydroxyethyl cellulose (HEC), hydroxymethyl cellulose (HMC), and hydroxymethylethyl cellulose (HMEC) indicated similar results.

In addition to the reactions with γ-cyclodextrin and amylose films, cryogenically milled polysaccharides in powder form were examined as an isooctane-insoluble substrate. The FTIR spectrum of the macromolecule in powder form following enzymatic reaction also showed evidence of acylation similar to that shown in FIGS. 1A and 1B. Derivatized powder α-cyclodextrin, β-cyclodextrin, chitosan, pullulan, maltodextrose, cellulose, hydroxypropyl cellulose (HPC), hydroxyethyl cellulose (HEC), hydroxymethyl cellulose (HMC), and hydroxymethylethyl cellulose (HMEC) showed carbonyl absorption in the FTIR spectra similar to that found for the acylated γ-cyclodextrin and amylose.

It is important to note that when subtilisin enzyme was used as a catalyst without ion pairing, no polysaccharides acylation occurred. Specifically, in the presence of 60 mM C10VE and 10 mg/ml of subtilisin powder, no evidence for derivatization was apparent when each polysaccharide was used in powder form or thin film deposited on ZnSe. Thus, the soluble enzyme form in the presence of AOT is required for acylation of the insoluble polymer.

Figure 2A:
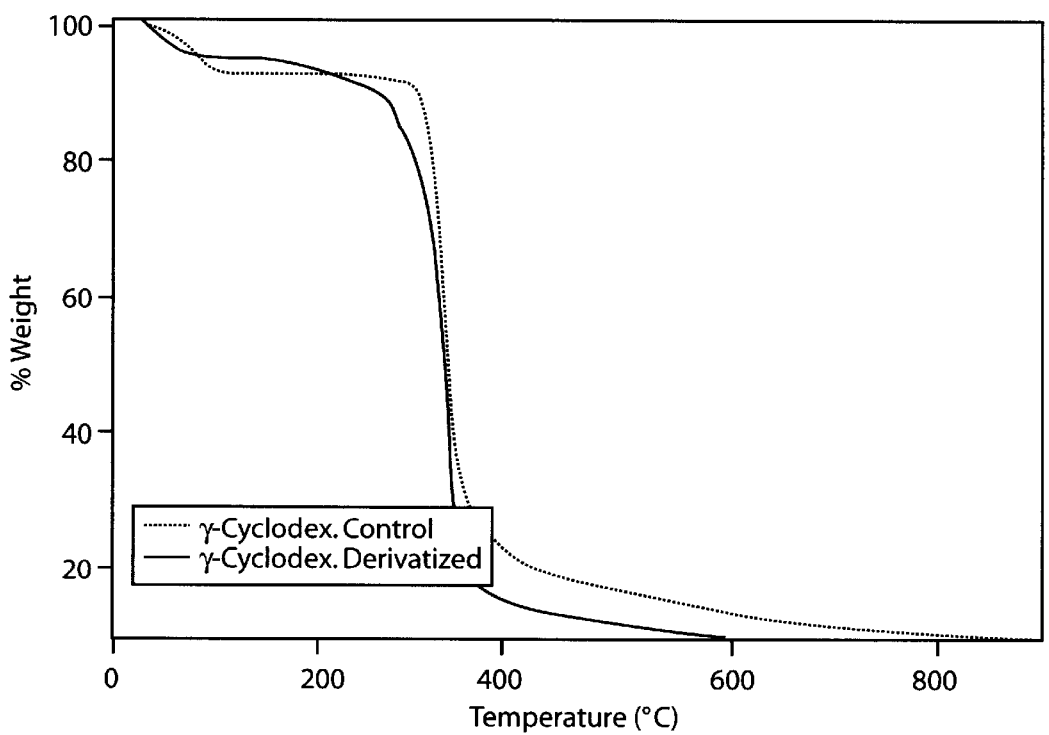
FIG. 2A shows thermogravimetric analysis (TGA) of control and derivatized γ-cyclodextrin.
Figure 2B:
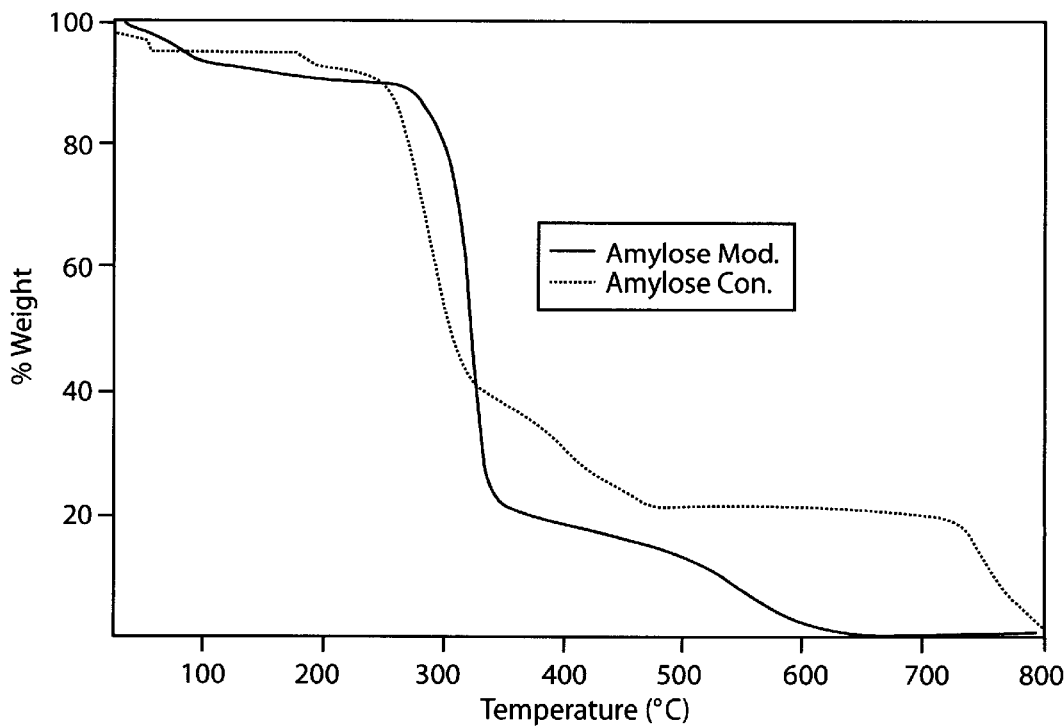
FIG. 2B shows TGA of control and derivatized amylose.
Figure 2C:
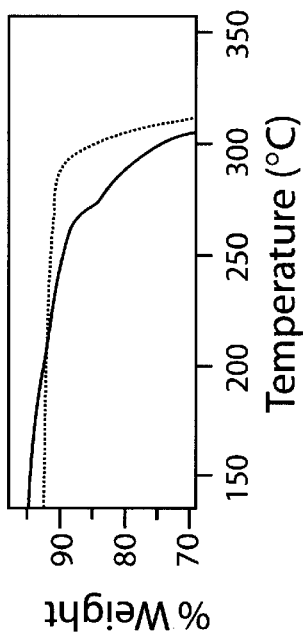
FIG. 2C shows a portion of the TGA of FIG. 2A enlarged to show more detail.

The degree of cyclodextrin and of amylose enzymatic acylation in the powder form was determined by TGA and $^1$H-NMR. The TGA profiles for control γ-cyclodextrin and enzymatically acylated γ-cyclodextrin powder and for control amylose and enzymatically acylated amylose powder are shown in FIGS. 2A (and 2C) and 2B, respectively. The only significant difference between the modified and control γ-cyclodextrin preparations and of amylose preparations (prior to substantial thermal degradation) was the weight loss in the modified polymer at 255° C. and 198° C., respectively, which is characteristic of alkyl chain degradation.[9] The weight loss of the modified γ-cyclodextrin reacted in powder form compared to the native polymer indicated that on the average 0.15 acyl chains were associated with each glucose moiety in the powder form. Comparable results were found for modified α-cyclodextrin (0.21), β-cyclodextrin (0.18), and amylose (0.15).[7] Derivatized chitosan, pullulan, maltodextrose, cellulose, hydroxypropyl cellulose (HPC), hydroxyethyl cellulose (HEC), hydroxymethyl cellulose (HMC), and hydroxymethylethyl cellulose (HMEC) had, also, equivalent results.

It is important to note that non regioselective chemical acylation of cyclodextrins (α-, β-, and γ-), and amylose (using acyl chlorides) show analogous TGA, and FTIR results as the enzymatically-treated polymers, but regioselectivity is lost by chemical acylation.

ESCA analysis of the first 100 Å of amylose thin film indicates that the acylated surface had a degree of substitution of 0.9±0.1 acyl chains per glucose moiety and this corresponded well to the expected regioselectivity of subtilisin catalysis on glucose-containing compounds.

All three cyclodextrins and the amylose contain free hydroxyls at the C-2, C-3, and C-6 positions, the latter being a primary hydroxyl. $^1$H-NMR was used to determine the site of enzymatic acylation of the three cyclodextrins and of the amylose. In comparison to underivatized cyclodextrins and to underivatized amylose, significant changes in area occurred in the β-cyclodextrin at C-2 and C-3 hydroxyls, and in γ-cyclodextrin and amylose at the C-6 hydroxyl position. For the α-cyclodextrin, the acylation was not selective. $^1$H-NMR of the enzymatically modified amylose, α-, β-, and γ-cyclodextrin powders generates peaks at 0.8 and 1.2 ppm, representing $CH_3$ and $CH_2$ protons, respectively, confirming the presence of fatty acid alkyl moiety on the derivatized cyclodextrins. These groups do not exist in the control amylose or cyclodextrins.

$^1$H-NMR (DMSO-d6) data for α-cyclodextrin:
control α-cyclodextrin: δ3.3–3.8 (2 H, 3 H, 4 H, 6 H, br), 4.2 (6 H, m), 4.4 (6 OH, m, area 0.505), 4.85 (1 H, br, area 0.512), 5.4 (3 OH, br, area 0.500), 5.5 (2 OH, br, area 0.500);
derivatized α-cyclodextrin: δ0.8 ($CH_3$, br), 1.2 ($CH_2$, br), 1.3 ($CH_2$, br), 2.2 ($CH_2$, br), 3.3–3.8 (2 H, 3 H, 4 H, 6 H, br), 4.35 (6 OH, m, area 0.5037), 5.2 (1 H, br, area 0.5612), 5.4 (3 OH, br, area 0.501), 5.45 (2 OH, br, area 0.500).

The ratio of proton peak area for a specific hydroxyl group (2 OH, 3 OH or 6 OH) to the summed area of the protons for [(1 H+2 OH+3 OH+6 OH)–(the proton area of the specific hydroxyl group )] is the same (~2.99) in the unreacted α-cyclodextrin. Upon enzymatic reaction, the ratios change to ~3.101 for all three hydroxyl sites, indicative of nonselective acylation.

Enzymatic specificity for β-cyclodextrin was demonstrated by $^1$H-NMR (DMSO-d6):
control β-cyclodextrin: δ3.2–3.7 (2 H, 3 H, 4 H, 6 H, br), 4.38 (6 OH, m, area 0.535), 4.85 (1 H, br, area 0.525), 5.65 (3 OH, br, area 0.50), 5.7 (2 OH, br, area 0.50);
derivatized β-cyclodextrin: δ0.82 ($CH_3$, br), 1.25 ($CH_2$, br), 1.3 ($CH_2$, br), 2.2 ($CH_2$, br), 3.1–3.7 (2 H, 3 H, 4 H, 6 H, br), 4.35 (6 OH, m, area 0.541), 4.85 (1 H, br, area 0.5645), 5.60 (3 OH, br, area 0.499), 5.65 (2 OH, br, area 0.501).

The ratio of proton peak area for a specific hydroxyl group (2 OH, 3 OH or 6 OH) to the summed area of the protons for [(1 H+2 OH+3 OH+6 OH)–(the proton area of the specific hydroxyl group )] is the same (~2.9) in the unreacted β-cyclodextrin. Upon enzymatic reaction, the ratios change to ~3.21 for 2 OH and 3 OH, and ~2.89 for 6 OH. This indicates selective substitution at 2 OH and 3 OH, with no preference between these two sites.

Regioselectivity for γ-cyclodextrin was demonstrated by $^1$H-NMR (DMSO-d6):
control γ-cyclodextrin: δ3.15–3.7 (2 H, 3 H, 4 H, 6 H, br), 4.4 (6 OH, m, area 0.5131), 4.88 (1 H, br, area 0.5135), 5.65 (3 OH, br, area 0.50), 5.7 (2 OH, br, area 0.50);
derivatized γ-cyclodextrin: δ0.84 ($CH_3$, br), 1.25 ($CH_2$, br), 1.3 ($CH_2$, br), 2.2 ($CH_2$, br), 3.2–3.7 (2 H, 3 H, 4 H, 6 H, br), 4.4 (6 OH, m, area 0.470), 4.88 (1 H, br, area 0.488), 5.62 (3 OH, br, area 0.499), 5.66 (2 OH, br, area 0.501).

The ratio of proton peak area for a specific hydroxyl group (2 OH, 3 OH or 6 OH) to the summed area of the protons for [(1 H+2 OH+3 OH+6 OH)–(the proton area of the specific hydroxyl group )] is the same (~3.0) in the unreacted γ-cyclodextrin. Upon enzymatic reaction, the ratios change to ~3.17 for 6 OH, and ~2.95 for 2 OH and 3 OH, indicative of selective substitution at 6 OH.

Integration of the alkyl chain protons of γ-cyclodextrin, β-cyclodextrin, and α-cyclodextrin protons resulted in a calculated degree of substitution of 0.28, 0.25, and 0.30, respectively.[10] These values are slightly different than those predicted by TGA analysis of the powdered amylose. This discrepancy may be the result of the qualitative nature of TGA analysis as compared to $^1$H-NMR.

Enzymatic specificity for amylose is demonstrate by $^1$H-NMR (DMSO-d6):
native amylose: δ3.8 (2 H, 3 H, 4 H, 6 H, br), 4.3 (6 H, m), 4.5 (6 OH, m, area 0.348), 4.9 (1 H, ax, m), 5.2 (1 H, br, area 0.336), 5.5 (3 OH, br, area 0.330), 5.6 (2 OH, br, area 0.330);
derivatized amylose: δ0.8 ($CH_3$, br), 1,2 ($CH_2$, br), 1.3 ($CH_2$, br), 2.2 ($CH_2$, br), 3.75 (2 H, 3 H, 4 H, 6 H, br), 4.4 (6 OH, m, area 0.467), 5.2 (1 H, br, area 0.509), 5.4 (3 OH, br, area 0.495), 5.45 (2 OH, br, area 0.495).

Note shift of 6-OH proton in the derivatized amylose. Furthermore, note that the area ratio of 6-OH proton to total protons in the native and derivatized amylose is 0.26 and 0.23, respectively. This provide additional evidence that acylation was confined at the 6-OH group. Integration of the alkyl chain protons and the amylose protons resulted in a calculated degree of substitution of 0.185. This is slightly lower than that predicted by TGA analysis of the powdered amylose. Such a discrepancy may result from the relatively qualitative nature of TGA analysis as compared to $^1$H-NMR. Parallel results were found for chitosan, pullulan, maltodextrose, cellulose, hydroxypropyl cellulose (HPC), hydroxyethyl cellulose (HEC), and hydroxymethyl cellulose (HMC).

The results for enzymatic transesterification show a non-selective substitution for the α-cyclodextrin, while selective acylation was observed for the secondary alcohol (β-cyclodextrin) and primary alcohol (γ- cyclodextrin and amylose), respectively, as postulated by the reaction shown in FIG. 3.

Furthermore, reactions of chitosan, α-cyclodextrin, and hydroxyethyl cellulose (HEC) were carried out in presence of adipic acid divinyl ester (C6DVE). Here chitosan is reported as an example.

Figure 4:
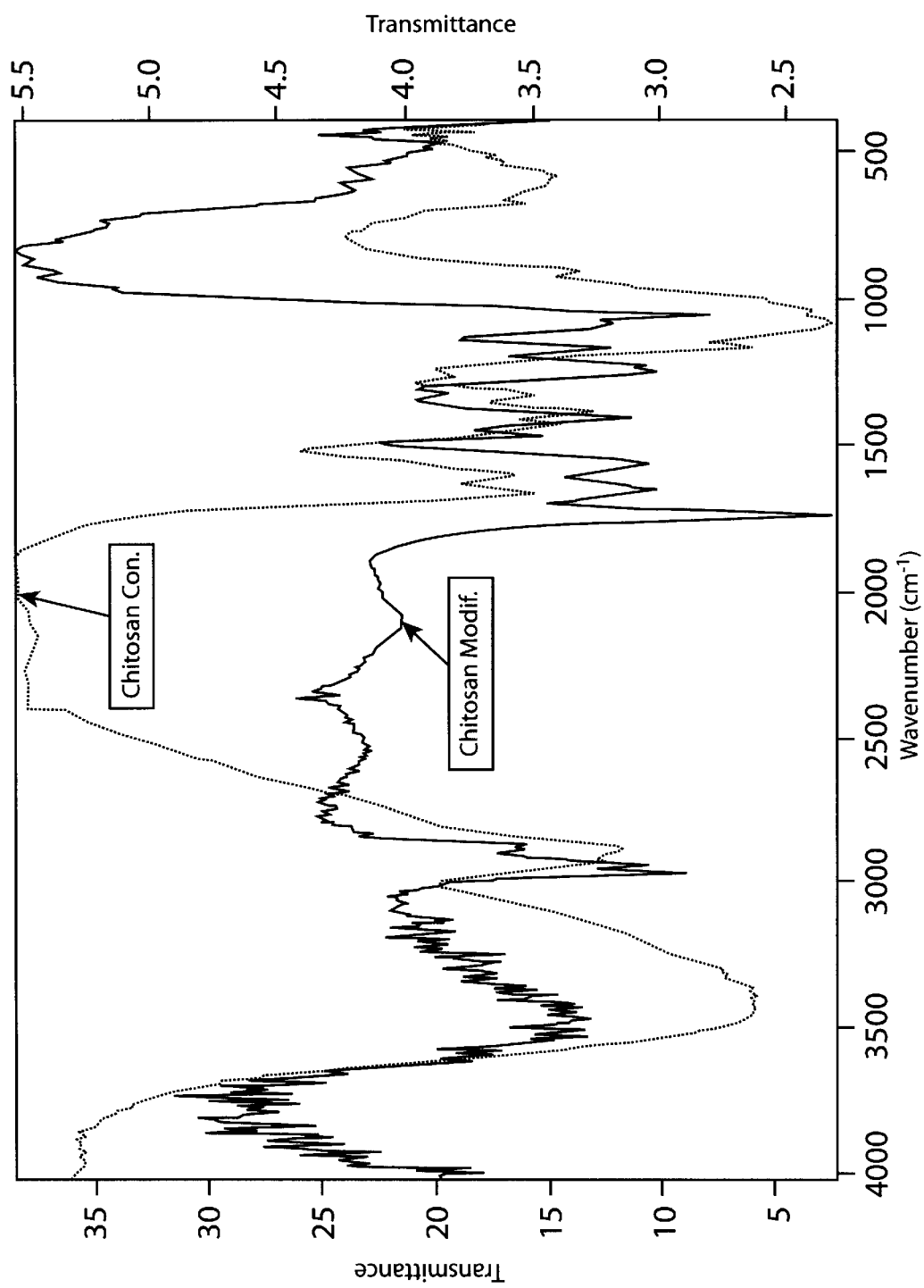
FIG. 4 shows the crosslinking of chitosan using divinyl esters of fatty acids.

As depicted in FIG. 4, the enzymatic acylation resulted in a crosslinked chitosan with a spectrum that contained peaks in the region 1693–1760 $cm^{-1}$, attributed to a C=) group, as well as peaks centered in the region 1399–1401 $cm^{-1}$, assigned to an amide group. These peaks were not present in the control samples.

It is important to underline that in the case of hydroxyethyl cellulose (HEC), a powder was formed after enzymatic reaction. Such powder gelled in the presence of solvents such as ethyl alcohol and dimethyl sulfone oxide (DMSO).

Superscripted reference numerals have been used throughout the preceding text to indicate reference sources. Those numerals correspond to the following references:

1. Mayer, J. M.; Kaplan, D. L.; 2 *Trends Polym. Sci.* 227 (1994).
2. Klibanov, A. M.; 14 *Trends Biochem. Sci.,* 141 (1989).
3. Klibanov, A. M.; 23 *Acc. Chem. Res.,* 114 (1990).
4. Dordick, J. S.; 11 *Enzyme Microb. Technol.* 194 (1989).
5. Kuhl, P.; Haling P. J.; Jakubke, H. D. 31 *Tetrahedron Lett.,* 5213 (1990).
6. Gill, I.; Vulfson, E.; 115 *J. Am. Chem. Soc.,* 3348 (1994).
7. Bruno, F. F.; Akkara, J. A.; Kaplan, D. L.; Gross, R.; Swift G.; Dordick, J. S.; 28 *Macromolecules* 8881 (1995).
8. Paradkar, V. M.; Dordick, J.; 116 *J. Am. Chem Soc.,* 5009 (1994).
9. Lukaszewski, G. M.; 15 *Lab. Practice,* 551 (1966).
10. T. Itoh, Y. Tsujii, H. Suzuki, T. Fukuda, T. Miyamoto; 24 *Polym. J.* 641 (1992).

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

What is claimed is:

1. An esterified organic solvent-insoluble macromolecule, made by:
    (a) solubilizing an enzyme in a volume of hydrophobic organic solvent provided with a surfactant by formation of enzyme-surfactant ion pairs,
    (b) initiating an esterification reaction by addition to the volume of hydrophobic organic solvent containing the solubilized enzyme of
        (i) a macromolecule to be esterified having at least one hydroxyl group available for esterification and
        (ii) a molar excess, relative to the number of macromolecule hydroxyl groups available for esterification of an acyl group donor reagent,
    (c) allowing the esterification reaction to continue under incubation conditions, and
    (d) terminating the esterification reaction by washing the macromolecule with a volume of fresh hydrophobic organic solvent to remove any unreacted acyl donor reagent,
wherein the polysaccharide is esterified by adipic acid divinyl ester (C6DVE).

2. An esterified organic solvent-insoluble macromolecule, as claimed in claim 1, wherein the polysaccharide is selected from the group consisting of chitosan, α-cyclodextrin, and hydroxyethyl cellulose (HEC).

3. An esterified organic solvent-insoluble macromolecule, made by:
    (a) solubilizing an enzyme in a volume of hydrophobic organic solvent provided with a surfactant by formation of enzyme-surfactant ion pairs.
    (b) initiating an esterification reaction by addition to the volume of hydrophobic organic solvent containing the solubilized enzyme of
        (i) a macromolecule to be esterified having at least one hydroxyl group available for esterification and
        (ii) a molar excess, relative to the number of macromolecule hydroxyl groups available for esterification of an acyl group donor reagent,
    (c) allowing the esterification reaction to continue under incubation conditions, and
    (d) terminating the esterification reaction by washing the macromolecule with a volume of fresh hydrophobic organic solvent to remove any unreacted acyl donor reagent,
wherein the polysaccharide forms a gel upon esterification by adipic acid divinyl ester (C6DVE).

* * * * *